United States Patent
Morimoto et al.

(10) Patent No.: US 12,004,711 B2
(45) Date of Patent: Jun. 11, 2024

(54) ENDOSCOPE

(71) Applicant: FUJIFILM Corporation, Tokyo (JP)

(72) Inventors: Yasuhiko Morimoto, Kanagawa (JP); Tsuneo Fukuzawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 10 days.

(21) Appl. No.: 16/902,270

(22) Filed: Jun. 16, 2020

(65) Prior Publication Data

US 2020/0305691 A1 Oct. 1, 2020

Related U.S. Application Data

(63) Continuation of application No. PCT/JP2018/047060, filed on Dec. 20, 2018.

(30) Foreign Application Priority Data

Jan. 26, 2018 (JP) .................................. 2018-011752

(51) Int. Cl.
*A61B 1/00* (2006.01)
*A61B 1/05* (2006.01)
*A61B 1/12* (2006.01)

(52) U.S. Cl.
CPC ............ *A61B 1/00087* (2013.01); *A61B 1/05* (2013.01); *A61B 1/122* (2013.01)

(58) Field of Classification Search
CPC .............. A61B 1/0008; A61B 1/00087; A61B 1/00098; A61B 1/012; A61B 1/018;
(Continued)

(56) References Cited

U.S. PATENT DOCUMENTS 3,561,432 A * 2/1971 Yamaki .............. A61B 1/00188
600/167
6,432,090 B1 8/2002 Brunel
(Continued)

FOREIGN PATENT DOCUMENTS

CN 1775386 5/2006
CN 103908305 7/2014
(Continued)

OTHER PUBLICATIONS

"International Search Report (Form PCT/ISA/210) of PCT/JP2018/047060," dated Mar. 12, 2019, with English translation thereof, pp. 1-5.

(Continued)

*Primary Examiner* — Ryan N Henderson
*Assistant Examiner* — Pamela F Wu
(74) *Attorney, Agent, or Firm* — JCIPRNET

(57) ABSTRACT

There is provided is an endoscope that can improve the cleanliness of a peripheral portion of an elevator. An endoscope (1) includes an insertion part (12) that is provided with a treatment tool insertion channel (82), a distal end portion main body (36), an elevator housing portion (62) that is provided in the distal end portion main body (36) and is open in a first direction, a treatment tool outlet (80) that is open to an inside of the elevator housing portion (62) and communicates with the treatment tool insertion channel (82), and an elevator (60). The elevator (60) has a first surface (64) and a second surface (66) inside a facing region facing the treatment tool outlet (80) in a state where the elevator is positioned at an elevated position. The first surface (64) is provided to be inclined to an opening (58) side of the elevator housing portion (62) with respect to a direction of an axis (82A) of the treatment tool insertion channel (82), and the second surface (66) is provided to be inclined to an
(Continued)

opposite side to the opening (58) side of the elevator housing portion (62) with respect to the axis (82A) of the treatment tool insertion channel (82).

8 Claims, 9 Drawing Sheets

(58) Field of Classification Search
CPC ........... A61B 1/12; A61B 1/121; A61B 1/122; A61B 1/126; A61B 1/0125; A61B 1/00101; A61B 1/273
USPC .................. 600/104, 106, 107, 129, 170–171
See application file for complete search history.

(56) References Cited

U.S. PATENT DOCUMENTS

| | | | |
|---|---|---|---|
| 6,447,480 B1 | 9/2002 | Brunel | |
| 6,928,686 B2 | 8/2005 | Tomooka et al. | |
| 7,771,349 B2* | 8/2010 | Kohno | A61B 8/12 600/107 |
| 10,694,925 B2 | 6/2020 | Morimoto | |
| 2005/0222493 A1* | 10/2005 | Kohno | A61B 1/00098 600/117 |
| 2012/0078041 A1 | 3/2012 | Kitano et al. | |
| 2013/0331696 A1 | 12/2013 | Morimoto | |
| 2016/0116731 A1 | 4/2016 | Peters et al. | |
| 2017/0290566 A1* | 10/2017 | Hosogoe | A61B 8/12 |
| 2018/0092512 A1* | 4/2018 | Hiraoka | A61B 1/00098 |
| 2018/0153377 A1* | 6/2018 | Kodama | A61B 1/00101 |
| 2019/0223697 A1* | 7/2019 | Hosogoe | A61B 1/00101 |
| 2019/0328215 A1* | 10/2019 | Kolberg | A61B 1/00098 |

FOREIGN PATENT DOCUMENTS

| | | |
|---|---|---|
| CN | 106859577 | 6/2017 |
| CN | 107159787 | 9/2017 |
| CN | 107242849 | 10/2017 |
| CN | 108451484 | 8/2018 |
| JP | S6313101 | 1/1988 |
| JP | H05103757 | 4/1993 |
| JP | 2005287593 | 10/2005 |
| JP | 2013202197 | 10/2013 |
| JP | 2014046167 | 3/2014 |
| WO | 2011148894 | 12/2011 |

OTHER PUBLICATIONS

"Written Opinion of the International Searching Authority (Form PCT/ISA/237) of PCT/JP2018/047060," dated Mar. 12, 2019, with English translation thereof, pp. 1-7.

"Office Action of China Counterpart Application", dated Oct. 27, 2022, with English translation thereof, p. 1-p. 13.

\* cited by examiner

ENDOSCOPE

CROSS-REFERENCE TO RELATED APPLICATIONS

The present application is a Continuation of PCT International Application No. PCT/JP2018/047060 filed on Dec. 20, 2018 claiming priority under 35 U.S.C § 119(a) to Japanese Patent Application No. 2018-011752 filed on Jan. 26, 2018. Each of the above applications is hereby expressly incorporated by reference, in its entirety, into the present application.

BACKGROUND OF THE INVENTION

1. Field of the Invention

The present invention relates to an endoscope, and particularly to an endoscope comprising an elevator that elevates a treatment tool which is led out from an opening portion.

2. Description of the Related Art

In the related art, there is known an endoscope comprising an elevator and an elevator housing portion, which are in a distal end portion main body of an insertion part to be inserted into a body cavity. A treatment tool that is inserted into a treatment tool insertion channel to be led out from a treatment tool lead-out portion of the distal end portion main body is elevated by an elevator, and a lead-out direction in which the treatment tool is led out can be adjusted by changing an elevation angle of the elevator.

For example, JP2005-287593A discloses an endoscope in which an elevator is provided at a treatment tool lead-out portion, an elevating lever is connected to the elevator via a rotation shaft, an operation wire is connected to the elevating lever, and the operation wire is pushed and pulled through operation of an operation part installed consecutively to a proximal end portion of an insertion part.

SUMMARY OF THE INVENTION

It is necessary for an endoscope, which is inserted in a body cavity of a subject, to be cleaned each time. In a duodenoscope comprising an elevator, a distal end cap is attachable and detachable for the sake of easy cleaning, and the cleanliness in the vicinity of the elevator is ensured by removing the distal end cap. However, as in an ultrasonic endoscope, the attachable and detachable type distal end cap cannot be used in some cases, such as a case where an ultrasonic vibrator is provided on a distal end side and a liquid-tight structure of the ultrasonic vibrator is required. In such a case, cleaning the vicinity of the elevator can only be performed from an opening of an elevator housing portion using a cleaning tool such as a brush and a syringe, and the improvement in cleanliness of a back surface of the elevator is required.

In addition, although a chemical liquid is injected from an operation part side when cleaning the endoscope and the chemical liquid is discharged from a treatment tool outlet of a distal end portion to the elevator housing portion, in a case where the elevator is in front (side where the chemical liquid is discharged) of the treatment tool outlet, the chemical liquid which has hit the elevator leaks to the outside of the endoscope from the opening portion as it is. Thus, improving the cleanliness of the vicinity of a rotation shaft of an elevating mechanism of the elevator is required.

The present invention is devised in view of such circumstances, and an object thereof is to provide an endoscope that can improve cleanliness of the endoscope, in particular, cleanliness of an elevating mechanism.

According to an aspect of the present invention, in order to achieve the object of the present invention, there is provided an endoscope comprising an insertion part that is provided with a treatment tool insertion channel, a distal end portion main body that is provided at a distal end of the insertion part, an elevator housing portion that is provided in the distal end portion main body and is open in a first direction perpendicular to an axial direction of the distal end portion main body, a treatment tool outlet that is open to an inside of the elevator housing portion and communicates with the treatment tool insertion channel, and an elevator that is disposed inside the elevator housing portion and is provided to be rotatable about a rotation shaft between an elevated position and a fallen position. The elevator has a first surface and a second surface inside a facing region facing the treatment tool outlet in a state where the elevator is positioned at the elevated position. When seen from a rotation shaft direction of the elevator, the first surface is provided to be inclined to an opening side of the elevator housing portion with respect to an axial direction of the treatment tool insertion channel, and the second surface is provided to be inclined to an opposite side to the opening side of the elevator housing portion with respect to the axial direction of the treatment tool insertion channel.

According to the aspect of the present invention, when the elevator which is in a state positioned at the elevated position is projected on a plane orthogonal to the axial direction of the treatment tool insertion channel, it is preferable that out of surfaces forming the elevator, the first surface and the second surface are surfaces disposed inside a region where the treatment tool outlet is formed.

According to the aspect of the present invention, in a state where the elevator is positioned at the fallen position, it is preferable that the second surface is disposed outside the facing region.

According to the aspect of the present invention, when seen from the rotation shaft direction of the elevator, it is preferable that the second surface is disposed on a distal end side in the axial direction of the distal end portion main body from the rotation shaft in a case where the elevator is positioned at the fallen position.

According to the aspect of the present invention, it is preferable that the distal end portion main body has a cleaning communication hole which is formed by penetrating a bottom wall portion on an opposite side to the opening side of the elevator housing portion.

According to the aspect of the present invention, it is preferable that the distal end portion main body has, around the cleaning communication hole, a counterbore portion which is recessed such that a syringe for supplying a cleaning liquid to the elevator housing portion is able to be fitted therein.

According to the aspect of the present invention, it is preferable that the distal end portion main body has an observation window of which a position in the first direction is disposed on the opening side of the elevator housing portion when the distal end portion main body is projected on a plane orthogonal to the axial direction of the distal end portion main body.

According to the aspect of the present invention, it is preferable that the observation window is disposed on a proximal end side in the axial direction of the distal end portion main body from the elevator housing portion.

According to the aspect of the present invention, it is preferable that the observation window is disposed to be offset from the elevator housing portion in a second direction perpendicular to the first direction.

According to the aspect of the present invention, it is preferable that an ultrasonic transducer that has a plurality of ultrasonic vibrators on a distal end side of the distal end portion main body is comprised.

In the endoscope of the aspect of the present invention, since a cleaning liquid discharged from the treatment tool outlet can be introduced to flow to the opening side of the elevator housing portion and a rotation shaft side of the elevator, an elevating mechanism (rotation shaft) can be reliably cleaned.

DESCRIPTION OF THE PREFERRED EMBODIMENTS

Hereinafter, an endoscope according to an embodiment of the present invention will be described with reference to the accompanying drawings.

(Endoscope)

Figure 1:
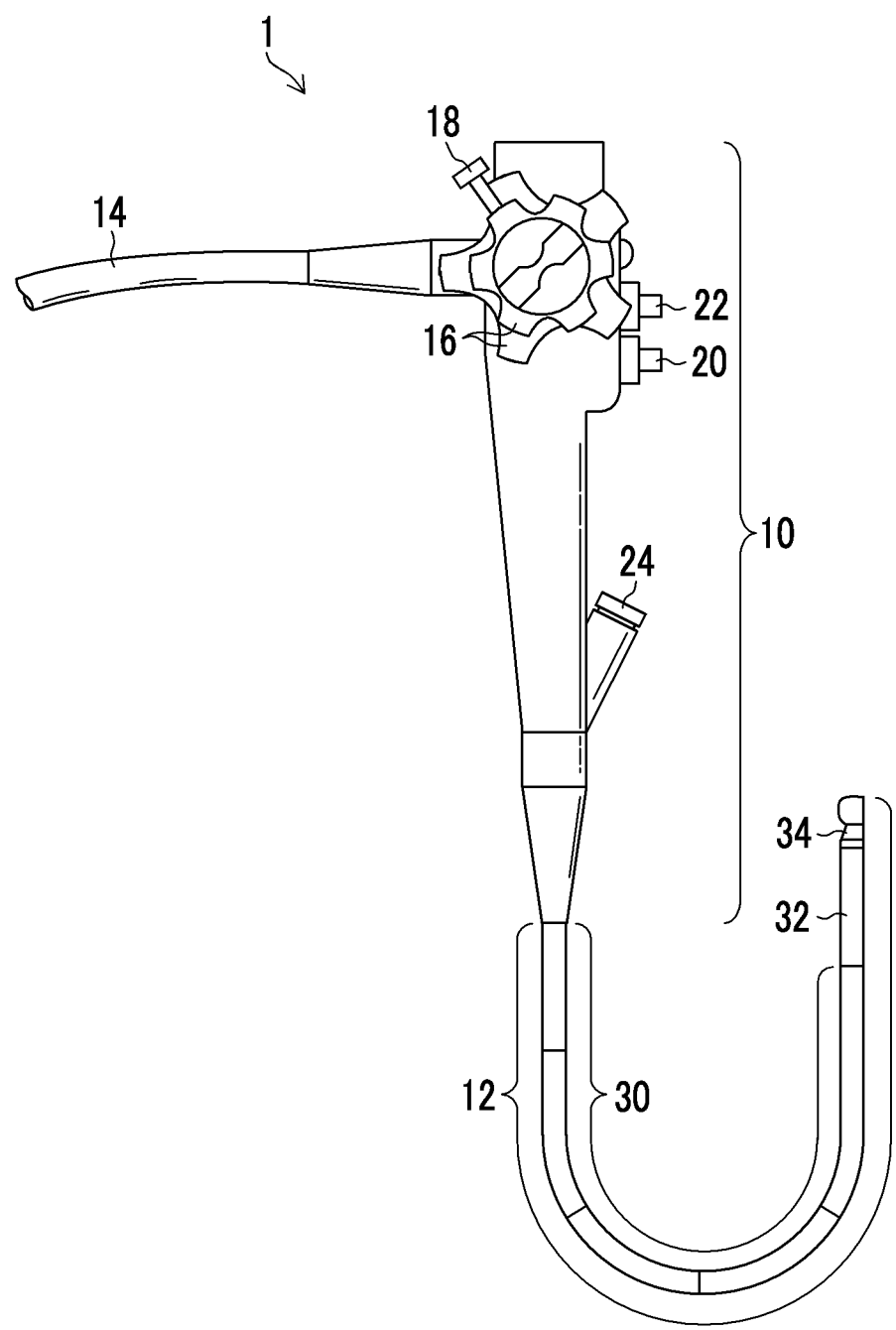
FIG. 1 is an overall view of an ultrasonic endoscope according to the embodiment of the present invention.

FIG. 1 is an overall view of an endoscope 1 to which the present invention is applied. Although an ultrasonic endoscope will be described as an example in the following embodiment, the present invention can also be applied to an endoscope other than the ultrasonic endoscope. That is, the present invention can be applied to an endoscope having an elevator and an elevating mechanism.

The endoscope 1 illustrated in FIG. 1 is configured by an operation part 10 that is gripped by a surgeon to perform various types of operation, an insertion part 12 that is inserted into a body cavity of a patient, and a universal cord 14. The endoscope 1 is connected to system configuring devices such as a processor device and a light source device (not illustrated) that configure an endoscope system via the universal cord 14.

The operation part 10 is provided with various types of operation members operated by a surgeon, for example, an angle knob 16, an elevating operation lever 18, an air supply and water supply button 20, and a suction button 22, of which workings will be described later as appropriate.

In addition, the operation part 10 is provided with a treatment tool inlet 24 through which a treatment tool is inserted into a treatment tool insertion channel inserted in the insertion part 12.

The insertion part 12 extends from a distal end of the operation part 10 and is formed to have a small diameter and an elongated shape as a whole.

In addition, the insertion part 12 is configured by a flexible portion 30, a curving portion 32, and a distal end portion 34 in order from a proximal end side to a distal end side.

The flexible portion 30 occupies most of the insertion part 12 from the proximal end side, and has flexibility allowing to be curved in any direction. In a case where the insertion part 12 is inserted in the body cavity, the flexible portion 30 curves along an insertion passage into the body cavity.

The curving portion 32 curves in an up-and-down direction and a right-and-left direction through rotating operation of the angle knob 16 of the operation part 10. The distal end portion 34 can be directed in a desired direction as the curving portion 32 curves.

As will be described in detail later with reference to FIGS. 2 to 4, the distal end portion 34 comprises an ultrasonic transducer 50 having a plurality of ultrasonic vibrators and a distal end portion main body 36 installed consecutively to the proximal end side of the ultrasonic transducer 50. In addition, the distal end portion main body 36 is provided with an elevator housing portion 62, and the elevator housing portion 62 has an opening portion 58 that is open in a first direction perpendicular to a direction of an axis 38 of the distal end portion main body 36. Further, the distal end portion main body 36 is provided with a treatment tool outlet 80, which is open to an inside of the elevator housing portion 62 and through which the treatment tool is led out. In addition, an elevator 60 that changes a lead-out direction in which the treatment tool is led out from the treatment tool outlet 80 is provided inside the elevator housing portion 62. The axis 38 of the distal end portion main body 36 refers to a line that matches or is parallel to an axis in a longitudinal direction of the insertion part 12 of FIG. 1.

The universal cord 14 illustrated in FIG. 1 includes an electric cable, a light guide, and a fluid tube therein. The universal cord 14 comprises a connector at an end portion (not illustrated) thereof. By the connector being connected to a predetermined system configuring device that configures the endoscope system, such as a processor device and a light source device, power, a control signal, illumination light, a liquid, and a gas, which are necessary for operating the endoscope 1, are supplied from the system configuring device to the endoscope 1. In addition, data of an observation image acquired by an image pick-up unit and data of an ultrasound image acquired by the ultrasonic transducer are transmitted from the endoscope 1 to the system configuring device. The observation image and the ultrasound image, which are transmitted to the system configuring device, can be displayed on a monitor and can be observed by a surgeon.

(Configuration of Distal End Portion)

Next, a configuration of the distal end portion 34 of the insertion part 12 will be described. FIG. 2 is a perspective view illustrating the appearance of the distal end portion 34. FIG. 3 is a plan view (top view). FIG. 4 is a side cross-sectional view.

The distal end portion 34 has the distal end portion main body 36 that forms an outer wall and an internal partition wall, and each configuration component disposed in the distal end portion main body 36 is housed and held in the housing portion comprised in the distal end portion main body 36.

Although details are omitted, a part of the distal end portion main body 36 can be attachably and detachably removed as a separate block. In a state where the separate block is removed, respective configuration components can be assembled into a predetermined housing portion. After assembling the respective configuration components into the housing portion, the respective configuration components are housed and held in the housing portion and are fixed to the distal end portion 34 as the separate block is attached to the distal end portion main body 36.

The distal end portion main body 36 is formed of an insulating material having an insulating property, for example, a resin material such as a methacrylic resin and a plastic including polycarbonate.

Figure 2:
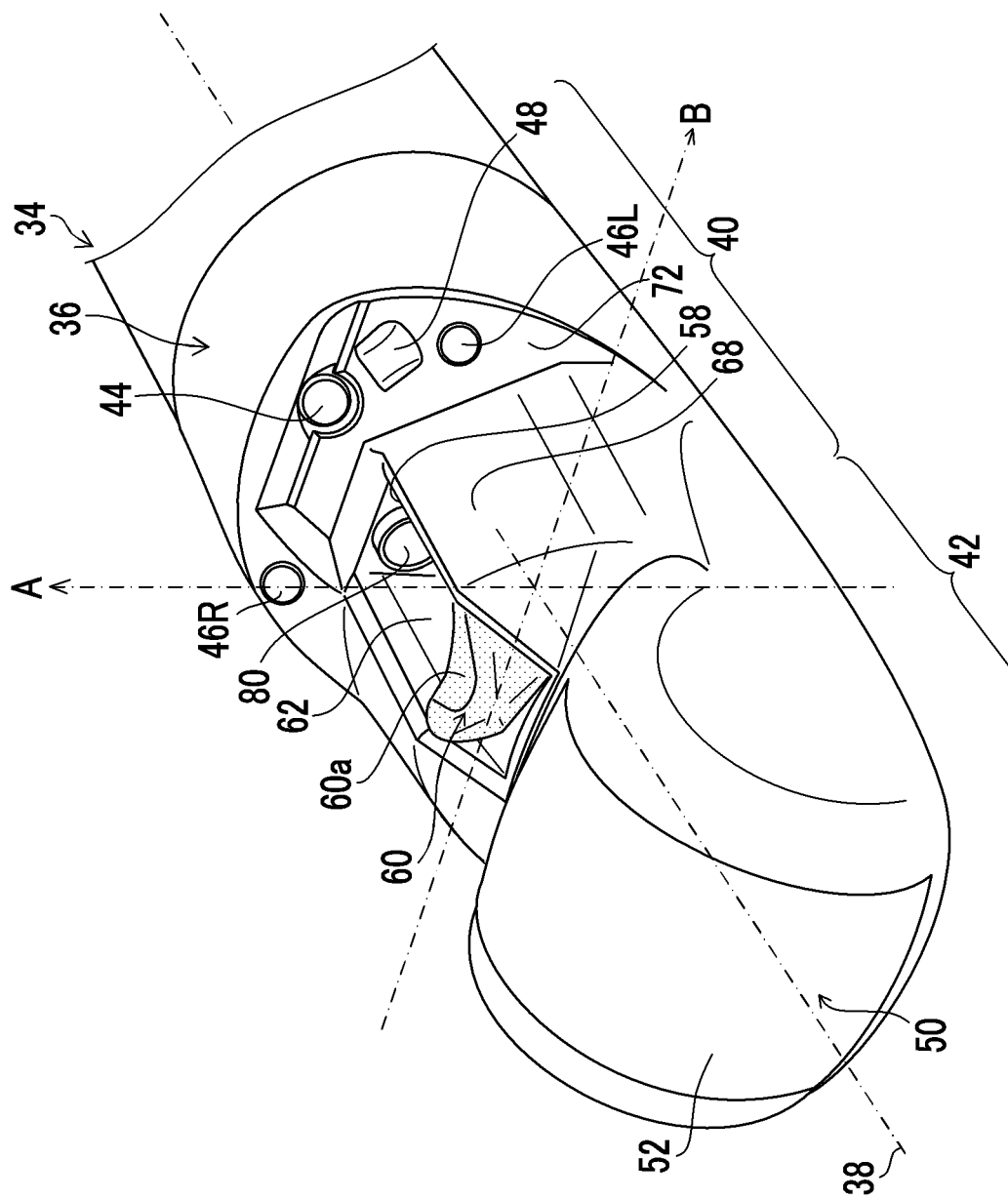
FIG. 2 is a perspective view illustrating an appearance of a distal end portion of an insertion part.
Figure 3:
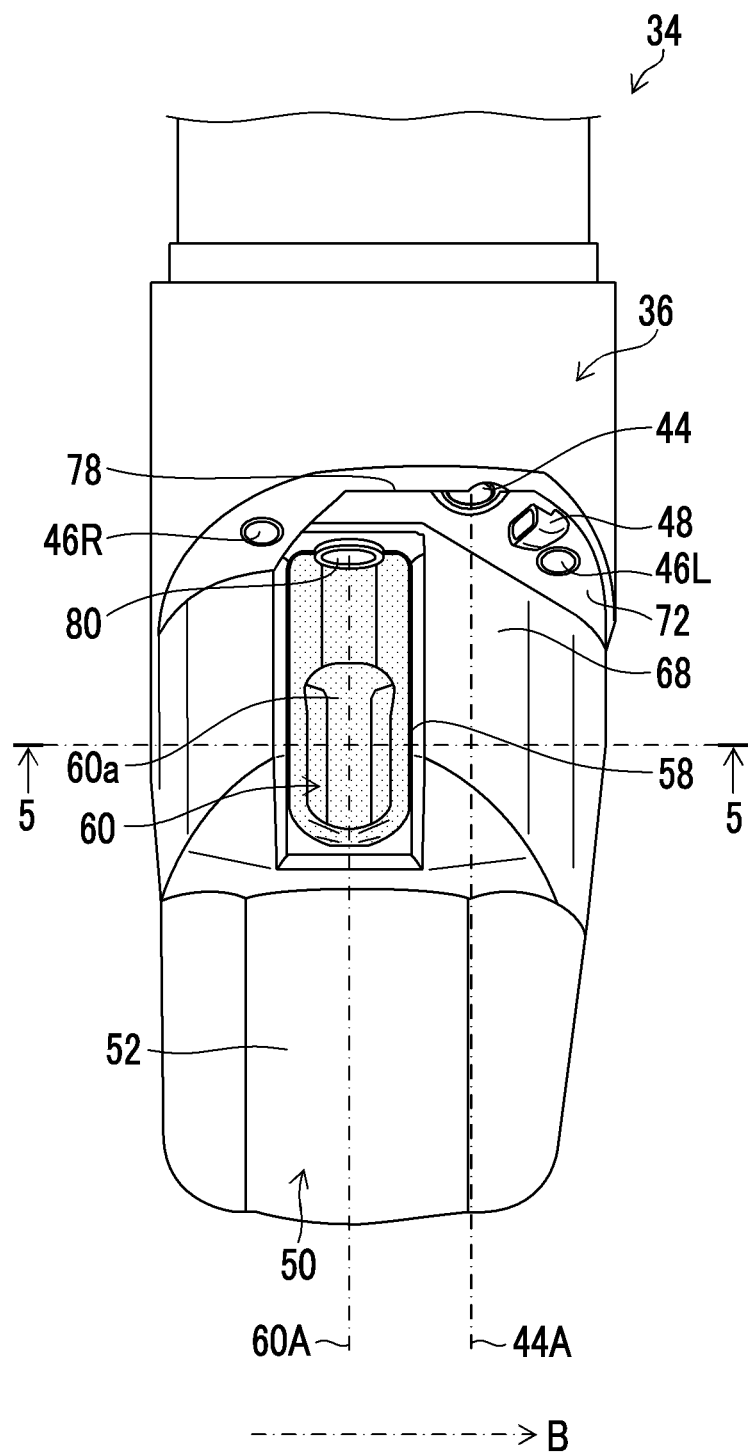
FIG. 3 is a plan view (top view) illustrating the appearance of the distal end portion of the insertion part.
Figure 4:
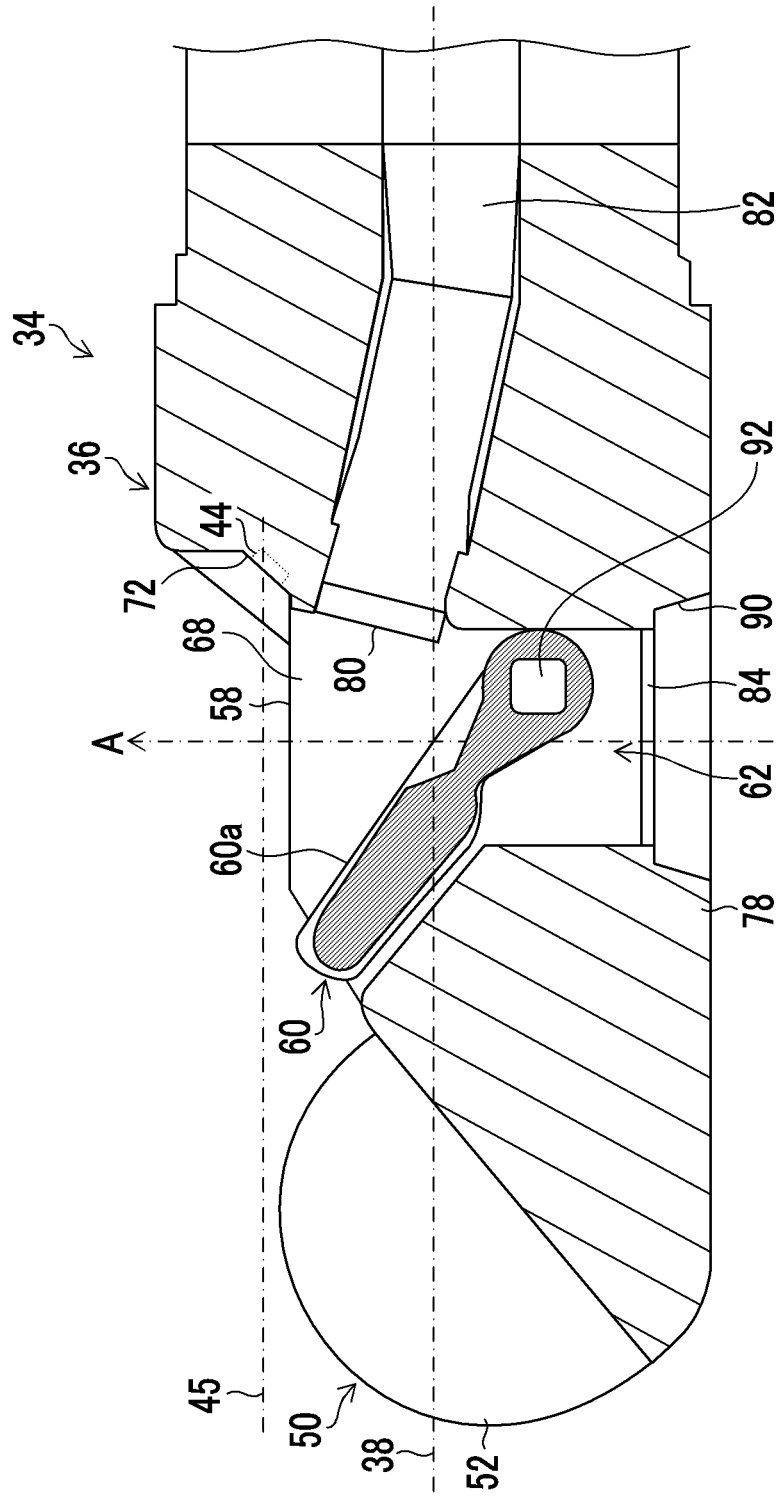
FIG. 4 is a side cross-sectional view illustrating the distal end portion of the insertion part.

The distal end portion 34 is configured by a base portion 40 configuring the distal end portion main body 36 as illustrated in FIGS. 2 to 4 and an extension portion 42 extending from the base portion 40 to the distal end side to hold the ultrasonic transducer 50.

That is, the convex ultrasonic transducer 50 having an ultrasonic wave transmitting and receiving surface 52 formed by arranging the ultrasonic vibrators for transmitting and receiving ultrasonic waves in a curved shape along the direction of the axis 38 of the distal end portion main body 36 is provided in the extension portion 42. The ultrasonic transducer 50 acquires data for generating an ultrasound image of a body tissue.

As illustrated in FIGS. 2 and 3, the distal end portion main body 36 is provided with an observation window 44, illumination windows 46L and 46R, an air supply and water supply nozzle 48, the opening portion 58 through which the treatment tool is led out, and a standing wall portion 68 provided around the opening portion 58.

The opening portion 58 is provided in the base portion 40 of the distal end portion main body 36. The treatment tool is led out from the opening portion 58 into an ultrasonic scanning range of the ultrasonic transducer 50. The opening portion 58 of the elevator housing portion 62 provided in the distal end portion main body 36 is formed to be open in the first direction orthogonal to the direction of the axis 38 of the distal end portion main body 36. As illustrated in FIG. 2, the opening portion 58 may be formed such that a part thereof is obliquely inclined toward a lower side of the distal end side, or the opening portion 58 may be formed such that the entire part thereof is obliquely inclined. In the present specification, the "first direction" is a direction, which is perpendicular to the direction of the axis 38 of the distal end portion main body 36 and in which the opening portion 58 of the elevator housing portion 62 is formed, as shown with an arrow A of FIG. 4. In addition, as illustrated in FIG. 2, a "second direction" refers to a direction shown with an arrow B, which is perpendicular to the direction of the axis 38 of the distal end portion main body 36 and the first direction shown with the arrow A. In addition, "one side in the first direction" refers to a side where the opening portion 58 is open. In addition, in the present specification, the one side in the first direction will be referred to as "up" and "upward", and the other side in the first direction will be referred to as "down" and "downward" in some cases.

As illustrated in FIG. 4, the treatment tool outlet 80 that is open to the inside of the elevator housing portion 62 is disposed on the proximal end side of the elevator housing portion 62. The treatment tool outlet 80 communicates with the treatment tool inlet 24 of the operation part 10 (refer to FIG. 1) via a treatment tool insertion channel 82 inserted in the insertion part 12. Accordingly, when the endoscope is inserted into the body cavity to perform treatment or observation, the treatment tool inserted from the treatment tool inlet 24 is led out from the treatment tool outlet 80 (refer to FIG. 4) to the elevator housing portion 62. In addition, as a cleaning liquid is injected from the treatment tool inlet 24 when cleaning the endoscope, the cleaning liquid is discharged from the treatment tool outlet 80 into the elevator housing portion 62 through the treatment tool insertion channel 82.

The elevator 60 is disposed at a position of the elevator housing portion 62 in front of the treatment tool outlet 80. The elevator 60 is provided to be rotatable about a rotation shaft 92 between an elevated position and a fallen position. The elevator 60 is formed of a metal material such as stainless steel, and has a concave guide surface 60a on an upper surface side, which curves upward from the proximal end side to the distal end side of the distal end portion main body 36. The treatment tool, which is led out from the treatment tool outlet 80, is led out from the opening portion 58 above the elevator housing portion 62 to the outside upward with respect to the direction of the axis 38 of the distal end portion main body 36 (for example, a longitudinal axis direction of the insertion part 12) along the guide surface 60a.

In addition, through the operation of the elevating operation lever 18 illustrated in FIG. 1, the elevator 60 rotates about the rotation shaft 92 and performs an elevating operation. By causing the elevator 60 to perform an elevating operation to adjust an elevation angle from a fallen state, the lead-out direction in which the treatment tool is led out from the opening portion 58 (lead-out angle) can be changed.

The treatment tool insertion channel 82 illustrated in FIG. 4 is also connected to a suction channel (not illustrated), and can also suck a body fluid from the opening portion 58 as the suction button 22 of FIG. 1 is operated.

The observation window 44 is arranged in an observation means forming surface 72 provided on the proximal end side of the elevator housing portion 62. Inside the observation window 44, an imaging system unit, in which an imaging optical system and a solid image pickup element, which configure an image pick-up unit, are integrally assembled, is housed. Accordingly, in a case where light from a treatment unit, which is in a field of view of the image pick-up unit, enters from the observation window 44, the light is formed as an observation image on an individual imaging element via the imaging optical system. That is, an image of the treatment unit is picked up by the solid image pickup element.

The observation means forming surface 72, in which the observation window 44 is disposed, is configured by a surface having a normal component toward the distal end side in the direction of the axis 38 of the distal end portion main body 36. That is, the observation means forming surface 72 is formed as an inclined surface, which is inclined upward toward the proximal end side of the distal end portion 34. As the observation means forming surface 72 is set as a surface having the normal component toward the distal end side and the observation means forming surface 72 is provided with the observation window 44, the observation window 44 allows a position where the treatment tool is led out from the opening portion 58 to be in a field of view of the observation window 44. Therefore, the treatment tool from the opening portion 58 to a target treatment position can be checked through the observation window 44. The observation means forming surface 72 may be configured by a vertical surface perpendicular to the direction of the axis 38 of the distal end portion main body 36.

The illumination windows 46L and 46R are provided in the observation means forming surface 72 on both sides with the observation window 44 interposed therebetween. A light emission unit configuring an illumination unit is housed inside the illumination windows 46L and 46R. Illumination light transmitted from the light source device connected to the universal cord 14 via the light guide is emitted from the light emission unit, and the illumination light is emitted to the treatment unit in the field of view of the image pick-up unit via the illumination windows 46L and 46R.

The air supply and water supply nozzle 48 is provided in the observation means forming surface 72. Through operation of the air supply and water supply button 20 of FIG. 1, a cleaning liquid, water, or air (hereinafter, also referred to as the "cleaning liquid or the like") is jetted from the air supply and water supply nozzle 48 to the observation window 44 of FIG. 2, thereby cleaning the observation window 44.

As illustrated in FIG. 4, in the distal end portion main body 36, a bottom wall portion 78 on an opposite side to a side where the opening portion 58 of the elevator housing portion 62 is disposed comprises a cleaning communication hole 84 that allows the elevator housing portion 62 to communicate with the outside. Since a cleaning tool such as a brush and a syringe can be inserted from the cleaning communication hole 84 into the elevator housing portion 62 by providing the cleaning communication hole 84, a back surface side of the elevator 60 and a peripheral portion thereof can be easily cleaned.

Figure 5:
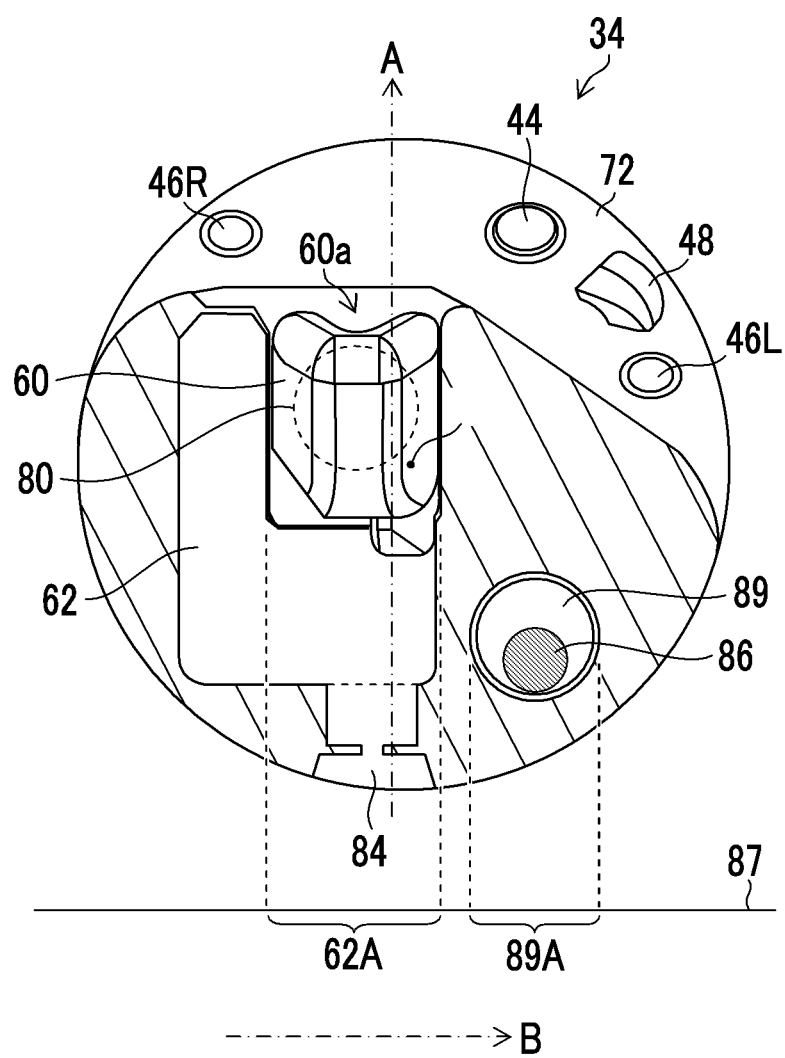
FIG. 5 is a cross-sectional view taken along line 5-5 in FIG. 3.

FIG. 5 is a cross-sectional view of the distal end portion main body 36 taken along line 5-5 in FIG. 3. A signal cable 86 is inserted into a cable insertion hole 89 and is arranged in the distal end portion main body 36. The signal cable 86 is a cable that connects the ultrasonic vibrators (not illustrated) of the ultrasonic transducer 50 illustrated in FIG. 2 to the system configuring devices. The signal cable 86 is arranged from the insertion part 12 to the universal cord 14 of FIG. 1. As illustrated in FIG. 5, when the cable insertion hole 89 and the elevator housing portion 62 are projected on an imaginary plane 87 perpendicular to the first direction shown with the arrow A, the cable insertion hole 89 is disposed in a region 89A that is different from a region 62A of the elevator housing portion 62. That is, when seen from the front, the cable insertion hole 89 and the elevator housing portion 62 are disposed side by side in the second direction as illustrated in FIG. 5. The cable insertion hole 89 is disposed on one side of the elevator housing portion 62 in the second direction (the right of the elevator housing portion 62 in FIG. 5). At this time, the elevator housing portion 62 is disposed on the other side in the second direction (the left from a center position C in FIG. 5) to be offset from the center position C of the distal end portion main body 36.

As described above, as the cable insertion hole 89 is disposed side by side with the elevator housing portion 62 in the second direction, the elevator housing portion 62 can be disposed on the lower side in the distal end portion main body 36. Since the elevator housing portion is disposed on the lower side, a distance from the cleaning communication hole 84 to the elevator 60 can be shortened, and the back surface side of the elevator 60 and the peripheral portion thereof can also be easily cleaned.

Next, a positional relationship among the opening portion 58, the elevator housing portion 62, and the observation window 44 will be described. In the embodiment, as illustrated in FIG. 5, as the elevator housing portion 62 is disposed on the lower side in the distal end portion main body 36, the positional relationship among the respective components configuring the distal end portion main body 36 can be set as follows.

As illustrated in FIG. 4, when a position of the opening portion 58 is set as a reference position, a position of the observation window 44 in the first direction (the up-and-down direction of FIG. 4) shown with the arrow A is disposed at a position on an opposite side to the elevator housing portion 62. That is, when the distal end portion main body 36 is projected on an imaginary plane orthogonal to the direction of the axis 38, the observation window 44 is disposed on an opening side (opening portion 58 side) of the elevator housing portion 62. As described above, as the observation window 44 is above the opening portion 58, the treatment tool can be put into an observation field of view of the observation window 44 at the position where the treatment tool is led out from the opening portion 58. Therefore, the treatment tool can be guided to a target position, and thus precision can be improved.

As for positions of the observation window 44 and the elevator housing portion 62 in the second direction, it is preferable to dispose the observation window 44 to be offset from the elevator housing portion 62 in the second direction shown with the arrow B, as illustrated in FIG. 3. Herein, disposing the observation window 44 to be offset from the elevator housing portion 62 in the second direction means that, for example, as illustrated in FIG. 3, when seen from above, a center line 44A of the observation window 44 is shifted from a center line 60A of the elevator 60 in the second direction shown with the arrow B. With such a configuration, even in a case where the elevator 60 is elevated and the treatment tool is led out from the opening portion 58, the observation field of view of the observation window 44 can be prevented from being blocked by the treatment tool and the elevator 60, and thereby the treatment position can be reliably checked through the observation window 44.

Figure 6:
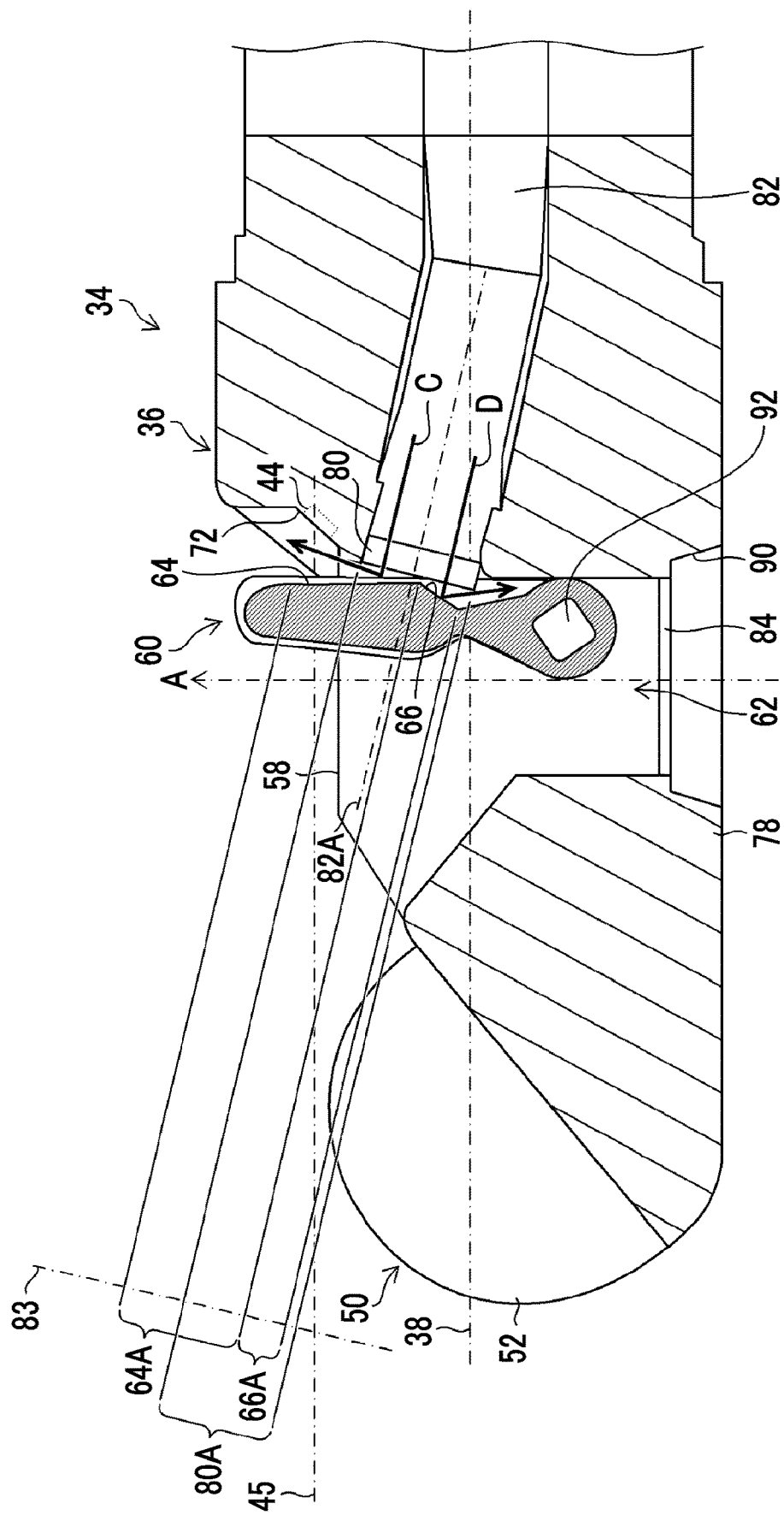
FIG. 6 is a side cross-sectional view of the distal end portion in a state where an elevator is at an elevated position.
Figure 7:
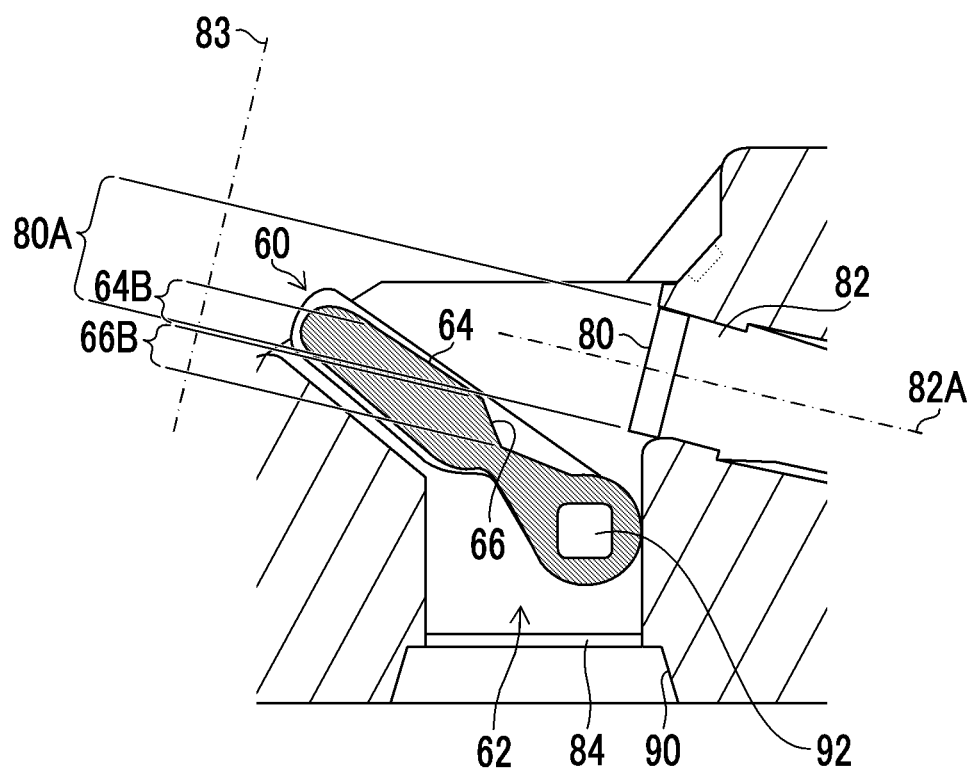
FIG. 7 is a side cross-sectional view in a state where the elevator is at a fallen position.

FIG. 6 is a cross-sectional view of a side surface of the endoscope in a state where the elevator is at the elevated position. FIG. 7 is a cross-sectional view of the side surface of the endoscope in a state where the elevator is at the fallen position.

In order to make a cleaning liquid discharged from the treatment tool outlet 80 flow not only to the opening side (opening portion 58 side) but also to a rotation shaft 92 side in the embodiment, a configuration including two surfaces such as a first surface 64 and a second surface 66 facing directions different from each other is adopted. In a state where the elevator 60 is at the elevated position, the first surface 64 and the second surface 66 are provided inside a facing region facing the treatment tool outlet 80. That is, as illustrated in FIG. 6, when the elevator 60, which is at the elevated position, and the treatment tool outlet 80 are projected on an imaginary plane 83 orthogonal to a direction of an axis 82A of the treatment tool insertion channel 82, at least a part of a region 64A of the first surface 64 and at least a part of a region 66A of the second surface 66 are disposed inside of a region 80A of the treatment tool outlet. As the first surface 64 and the second surface 66 are disposed as described above, both surfaces of the first surface 64 and the second surface 66 are disposed at positions that can be seen from the treatment tool outlet 80 when the elevator 60 which is at the elevated position is seen from the treatment tool outlet 80. In a state where the elevator 60 is at the elevated position, the first surface 64 and the second surface 66 are provided inside the facing region facing the treatment tool outlet 80. Thus, the cleaning liquid discharged from the treatment tool outlet 80 can hit the first surface 64 and the second surface 66.

Further, when the elevator 60 is seen from a rotation shaft direction, the first surface 64 is provided to be inclined toward the opening portion side 58 of the elevator housing portion 62 with respect to the direction of the axis 82A of the treatment tool insertion channel 82. In addition, the second surface 66 is provided to be inclined to an opposite side to the opening portion side 58 of the elevator housing portion 62 with respect to the direction of the axis 82A of the treatment tool insertion channel 82. That is, in a case where the elevator 60 is at the elevated position, the first surface 64 is formed obliquely upward with respect to the axis 82A of the treatment tool insertion channel 82, and the second surface 66 is formed obliquely downward with respect to the axis 82A of the treatment tool insertion channel 82. As the first surface 64 is provided to be inclined to the opening portion 58 side of the elevator housing portion 62, the cleaning liquid which has hit the first surface 64 can be introduced into the opening portion 58 side as shown with an arrow C of FIG. 6. In addition, as the second surface 66 is provided to be inclined to the opposite side to the opening portion 58 side of the elevator housing portion 62, that is, to an opposite side to the first surface 64, the cleaning liquid which has hit the second surface 66 can be introduced to the rotation shaft 92 side and the lower side of the elevator housing portion 62 as shown with an arrow D of FIG. 6. For this reason, the cleaning liquid discharged from the treatment tool outlet 80 can be supplied to the inside of the elevator housing portion 62, particularly, to a lower surface side of the elevator 60.

In addition, in a state where the elevator 60 is at the fallen position, the first surface 64 is disposed inside the facing region of the treatment tool outlet 80, and the second surface 66 is disposed outside the facing region of the treatment tool outlet 80. That is, in FIG. 7, when the elevator 60, which is at the fallen position, and the treatment tool outlet 80 are projected on the imaginary plane 83 orthogonal to the direction of the axis 82A of the treatment tool insertion channel 82, the first surface is disposed at a position where a region 64B of the first surface 64 and the region 80A of the treatment tool outlet 80 overlap each other. In addition, a region 66B of the second surface and the region 80A of the treatment tool outlet 80 are disposed at different positions. As the first surface 64 is disposed inside the facing region and the second surface 66 is disposed outside the facing region, the treatment tool led out from the treatment tool outlet 80 can be smoothly introduced to the first surface 64 of the elevator 60 with the elevator 60 at the fallen position. In addition, even in a case where the elevator 60 is moved to the elevated position and the fallen position in a state where the treatment tool is guided, the lead-out direction in which the treatment tool is led out can be changed well.

Figure 8:
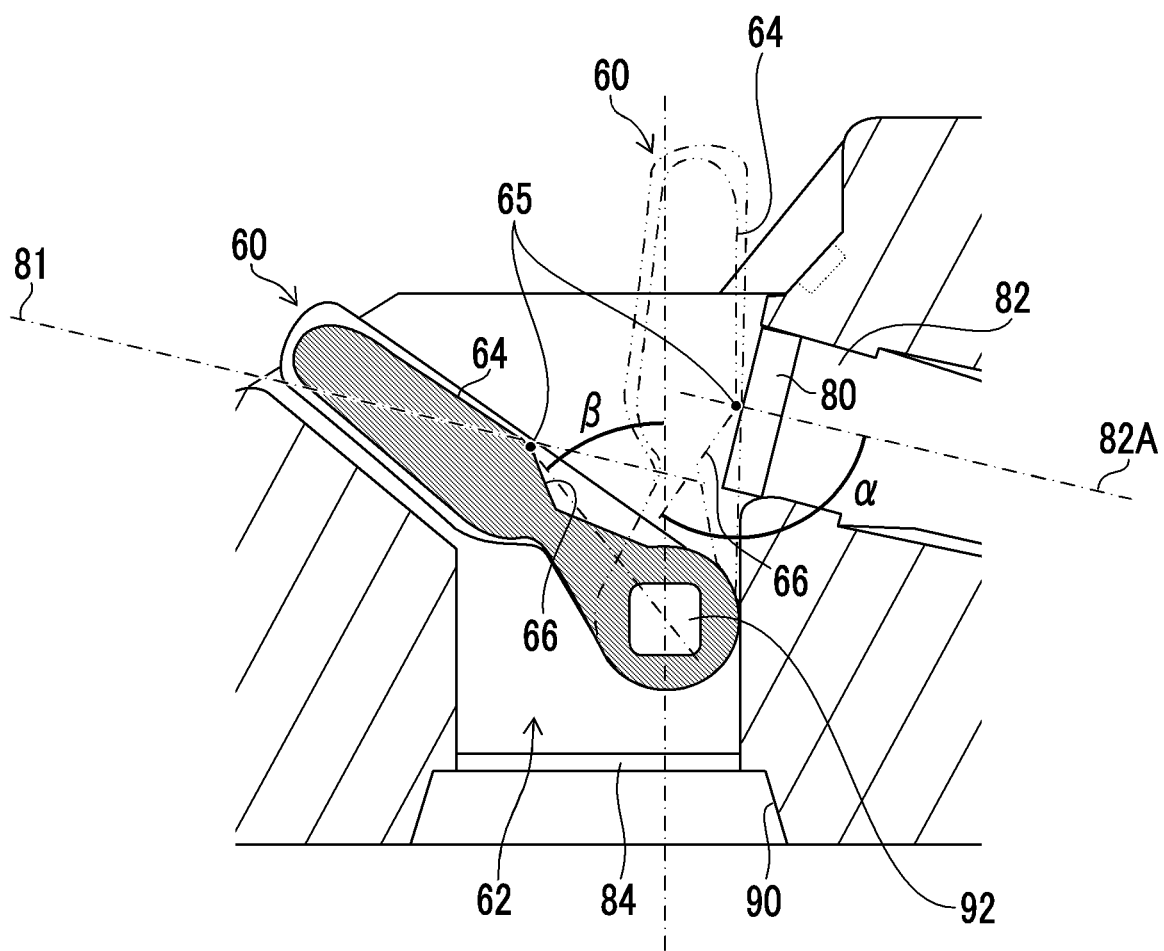
FIG. 8 is view illustrating a positional relationship between a treatment tool outlet and the elevator.

FIG. 8 is view illustrating a positional relationship between the treatment tool outlet 80 and the elevator 60. In FIG. 8, a state where the elevator 60 is at the fallen position is shown with a solid line, and a state where the elevator is at the elevated position is shown with a two-dot chain line.

In a state where the elevator 60 is at the elevated position, a branch point 65 which is a boundary between the first surface 64 and the second surface 66 is disposed above an imaginary line 81, which is obtained by extending a lower end of the treatment tool outlet 80 in the direction of the axis 82A of the treatment tool insertion channel 82. With such a configuration, the first surface 64 and the second surface 66 can be disposed inside the facing region of the treatment tool outlet 80 in an elevated state of the elevator 60, and a cleaning liquid can hit the first surface 64 and the second surface 66.

In addition, in a state where the elevator 60 is at the elevated position, an angle α between the second surface 66 and the axis 82A of the treatment tool insertion channel 82 is set to an angle larger than 90°. Accordingly, a cleaning liquid that has hit the second surface 66 is introduced to the rotation shaft 92 side, and the cleanliness of the rotation shaft 92 can be improved.

Further, when the elevator 60 has fallen, the branch point 65 is disposed below the imaginary line 81. In addition, an angle β formed between a line that connects the branch point 65 to a center point of the rotation shaft 92 and a line parallel to the first direction is 0° or more on the distal end side. With such a configuration, the treatment tool led out from the treatment tool outlet 80 can be smoothly introduced to the first surface 64 of the elevator 60.

Further, when seen from a direction of the rotation shaft 92 of the elevator 60 in a state where the elevator 60 is at the fallen position, it is preferable to dispose the second surface 66 of the elevator 60 on the distal end side in the direction of the axis 38 from the rotation shaft 92 of the elevator 60. As the second surface 66 is disposed on the distal end side from the rotation shaft 92 of the elevator 60, the second surface 66 can be disposed in the facing region when the elevator 60 is disposed at the elevated position.

Although the first surface 64 and the second surface 66 are formed to be directly connected to each other in the elevator 60 illustrated in FIGS. 6 to 8, the first surface and the second surface may be connected to each other via another surface therebetween insofar as the first surface and the second surface are included inside the facing region facing the treatment tool outlet 80, and with respect to the axial direction of the treatment tool insertion channel, the first surface is inclined to the opening side and the second surface is inclined to an opposite side thereto. In addition, the first surface 64 and the second surface 66 are not limited to flat surfaces. Even in a case where both or one of the first surface 64 or the second surface 66 is a curved surface, the first surface 64 and the second surface 66 may be formed as a smooth and continuous curved surface insofar as the cleaning liquid can be guided in each of directions.

Figure 9:
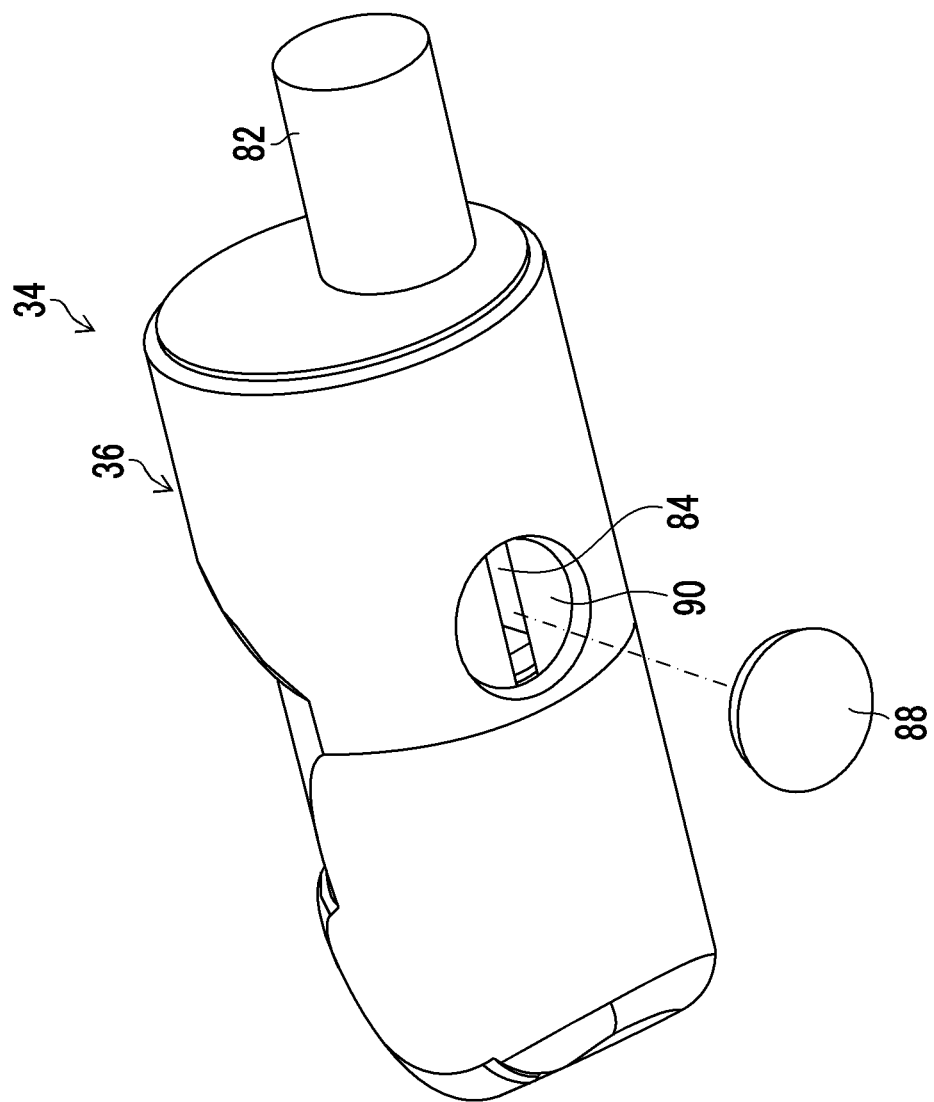
FIG. 9 is a bottom view of the distal end portion of the insertion part.

FIG. 9 is a bottom view of the distal end portion main body. As described above, the distal end portion main body 36 has the cleaning communication hole 84 that penetrates the bottom wall portion 78 of the elevator housing portion 62 and allows the elevator housing portion 62 to communicate with the outside. Further, a counterbore portion 90, which is recessed such that a syringe for supplying a cleaning liquid can be fitted therein, is provided around the cleaning communication hole 84. As the counterbore portion 90 is provided, the syringe for supplying the cleaning liquid (chemical liquid) can be fixed. Therefore, the syringe can be prevented from being shaken in a case of supplying the cleaning liquid, and the cleaning liquid can be reliably supplied to a predetermined position, for example, the elevator 60. The fixing of the syringe may be sufficient as long as a protection sheath of the syringe can be fixed at the counterbore portion 90 so as not to move. In addition, as a brush is inserted from the cleaning communication hole 84, a portion of the elevator 60 on an opposite side to the opening portion 58 can be easily cleaned.

In addition, as illustrated in FIG. 9, it is preferable for the distal end portion main body 36 to have a lid 88 which can be attached and detached to and from the cleaning communication hole 84. In a case of inserting the insertion part 12 of the endoscope 1 into a body cavity of a subject, the adhesion of dirt into the elevator housing portion 62 can be suppressed by mounting the lid 88 on the cleaning communication hole 84 and closing the cleaning communication hole 84. In addition, in a case of cleaning the elevator 60, the back surface side of the elevator and the peripheral portion thereof can be cleaned by the cleaning tool as the lid 88 is removed from the cleaning communication hole 84.

As described above, in the embodiment, the first surface 64 and the second surface 66 that configure the elevator 60 are disposed in the facing region of the treatment tool outlet 80 when the elevator 60 is elevated. The first surface 64 is provided to be inclined to the opening portion 58 side with respect to the direction of the axis 82A of the treatment tool insertion channel 82, and the second surface 66 is provided to be inclined to the opposite side to the opening portion 58. Accordingly, since a cleaning liquid discharged from the treatment tool outlet 80 can be introduced to the opening side of the elevator housing portion 62 with the first surface 64 and the second surface 66 and the rotation shaft 92 side of the elevator, an effect of improving the cleanliness of the elevating mechanism is obtained.

Although the convex ultrasonic transducer is described hereinbefore, the present invention is not limited to the convex ultrasonic transducer, and can also be applied to a radial ultrasonic transducer.

EXPLANATION OF REFERENCES

1: endoscope
10: operation part
12: insertion part
14: universal cord
16: angle knob
18: elevating operation lever
20: air supply and water supply button
22: suction button
24: treatment tool inlet
30: flexible portion
32: curving portion
34: distal end portion
36: distal end portion main body
38: axis of distal end portion main body
40: base portion
42: extension portion
44: observation window
44A: center line of observation window
45: axis of observation window
46L, 46R: illumination window
48: air supply and water supply nozzle
50: ultrasonic transducer
52: ultrasonic wave transmitting and receiving surface
58: opening portion
60: elevator
60A: center line of elevator
62, 62A: elevator housing portion
64, 64A, 64B: first surface
65: branch point
66, 66A, 66B: second surface
68: standing wall portion
72: observation means forming surface
78: bottom wall portion
80, 80A: treatment tool outlet
81: imaginary line
82: treatment tool insertion channel
82A: axis of treatment tool insertion channel
83, 87: imaginary plane
84: cleaning communication hole
86, 86A: signal cable
88: lid
89, 89A: cable insertion hole
90: counterbore portion
92: rotation shaft

What is claimed is:

1. An endoscope comprising:
an insertion part that is provided with a treatment tool insertion channel;
a distal end portion main body that is provided at a distal end of the insertion part;
an elevator housing portion that is provided in the distal end portion main body and is open in a first direction perpendicular to an axial direction of the distal end portion main body;
a treatment tool outlet that is open to an inside of the elevator housing portion and communicates with the treatment tool insertion channel, wherein the treatment tool outlet is disposed on a distal end of the treatment tool insertion channel; and
an elevator that is disposed inside the elevator housing portion and is provided to be rotatable about a rotation shaft between an elevated position and a fallen position,
wherein the elevator has a first surface and a second surface inside a facing region facing the treatment tool outlet in a state where the elevator is positioned at the elevated position, and
when seen from a rotation shaft direction of the elevator, the first surface is provided to be inclined to an opening side of the elevator housing portion with respect to an axial direction of the treatment tool insertion channel, and the second surface is provided to be inclined to an opposite side to the opening side of the elevator housing portion with respect to the axial direction of the treatment tool insertion channel,
wherein in a state where the elevator is positioned at the fallen position, the second surface does not overlap with the treatment tool outlet when seen from the axial direction of the treatment tool insertion channel,
wherein in the state where the elevator is positioned at the elevated position, the first surface and the second surface constitute a convex shape protruding toward the treatment tool outlet in the axial direction of the treatment tool insertion channel,
wherein the distal end portion main body has a cleaning communication hole which is formed by penetrating a bottom wall portion on an opposite side to the opening side of the elevator housing portion,
wherein the distal end portion main body has, around the cleaning communication hole, a counterbore portion which is recessed such that a syringe for supplying a cleaning liquid to the elevator housing portion is able to be fitted therein.

2. The endoscope according to claim 1,
wherein in the state where the elevator is positioned at the elevated position, the first surface and the second surface overlap with the treatment tool outlet when seen from the axial direction of the treatment tool insertion channel.

3. The endoscope according to claim 1,
wherein in the state where the elevator is positioned at the fallen position, the second surface is disposed outside the facing region.

4. The endoscope according to claim 1,
wherein when seen from the rotation shaft direction of the elevator, the second surface is disposed on a distal end side in the axial direction of the distal end portion main body from the rotation shaft in a case where the elevator is positioned at the fallen position.

5. The endoscope according to claim 1,
wherein the distal end portion main body has an observation window of which a position in the first direction is disposed on the opening side of the elevator housing portion when seen from the rotation shaft direction of the elevator.

6. The endoscope according to claim 5,
wherein the observation window is disposed on a proximal end side in the axial direction of the distal end portion main body from the elevator housing portion.

7. The endoscope according to claim 5,
wherein the observation window is disposed to be offset from the elevator housing portion in a second direction perpendicular to the first direction.

8. The endoscope according to claim 1, further comprising:
an ultrasonic transducer that has a plurality of ultrasonic vibrators on a distal end side of the distal end portion main body.

* * * * *